(12) United States Patent
Couture

(10) Patent No.: US 8,641,712 B2
(45) Date of Patent: Feb. 4, 2014

(54) LOCAL OPTIMIZATION OF ELECTRODE CURRENT DENSITIES

(75) Inventor: Gary M. Couture, Longmont, CO (US)

(73) Assignee: Covidien LP, Mansfield, MA (US)

( * ) Notice: Subject to any disclaimer, the term of this patent is extended or adjusted under 35 U.S.C. 154(b) by 753 days.

(21) Appl. No.: 12/845,203

(22) Filed: Jul. 28, 2010

(65) Prior Publication Data

US 2012/0029515 A1    Feb. 2, 2012

(51) Int. Cl.
*A61B 18/14* (2006.01)

(52) U.S. Cl.
USPC ............................................ 606/48; 128/898

(58) Field of Classification Search
USPC ..................... 128/898; 606/32–52
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| D402,028 S | 12/1998 | Grimm et al. |
| D416,089 S | 11/1999 | Barton et al. |
| D424,694 S | 5/2000 | Tetzlaff et al. |
| D425,201 S | 5/2000 | Tetzlaff et al. |
| D449,886 S | 10/2001 | Tetzlaff et al. |
| D454,951 S | 3/2002 | Bon |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

Wald et al., "Accidental Burns", JAMA, Aug. 16, 1971, vol. 217, No. 7, pp. 916-921.

(Continued)

*Primary Examiner* — Bill Thomson
*Assistant Examiner* — Jeffrey Lipitz
(74) *Attorney, Agent, or Firm* — Carter, DeLuca, Farrell & Schmidt, LLP

(57) ABSTRACT

An end effector assembly for use with a bipolar forceps includes a pair of opposing first and second jaw members at least one of which being movable relative to the other to grasp tissue therebetween. Each jaw member includes a pair of spaced apart, electrically conductive tissue sealing surfaces. Each tissue sealing surface is adapted to connect to a source of electrosurgical energy to conduct electrosurgical energy through tissue held therebetween to effect a tissue seal. The forceps also includes an insulator disposed between each pair of electrically conductive sealing surfaces and an electrically conductive cutting element disposed within each insulator and defining a geometrical configuration including a plurality of peaks having a period that is a multiple of an operating frequency of the electrosurgical energy. The cutting elements are adapted to connect to the source of electrosurgical energy to conduct electrosurgical energy through tissue held therebetween to effect a tissue cut.

13 Claims, 4 Drawing Sheets

(56) References Cited

U.S. PATENT DOCUMENTS

| | | |
|---|---|---|
| D457,958 S | 5/2002 | Dycus et al. |
| D457,959 S | 5/2002 | Tetzlaff et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,887,240 B1 | 5/2005 | Lands |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| 7,270,664 B2 | 9/2007 | Johnson et al. |
| 7,276,068 B2 | 10/2007 | Johnson |
| D564,662 S | 3/2008 | Moses et al. |
| D567,943 S | 4/2008 | Moses et al. |
| 7,354,440 B2 | 4/2008 | Truckal et al. |
| D574,323 S | 8/2008 | Waaler |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 2003/0139741 A1 | 7/2003 | Goble et al. |
| 2006/0116675 A1 | 6/2006 | McClurken et al. |
| 2007/0265616 A1 | 11/2007 | Couture et al. |
| 2008/0039835 A1 | 2/2008 | Johnson |
| 2008/0045947 A1 | 2/2008 | Johnson et al. |
| 2008/0058802 A1 | 3/2008 | Couture et al. |
| 2008/0195093 A1 | 8/2008 | Couture et al. |
| 2008/0249527 A1 | 10/2008 | Couture et al. |
| 2008/0294159 A1* | 11/2008 | Akahoshi et al. ........... 606/41 |
| 2010/0168741 A1 | 7/2010 | Sanai |
| 2010/0179543 A1 | 7/2010 | Johnson |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2602517 | 7/1976 |
| DE | 2504280 | 8/1976 |
| DE | 2514501 | 10/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3423356 | 6/1986 |
| DE | 3510586 | 10/1986 |
| DE | 3612646 | 4/1987 |
| DE | 3604823 | 8/1987 |
| DE | 8712328 | 3/1988 |
| DE | 390937 | 4/1989 |
| DE | 3904558 | 8/1990 |
| DE | 3942998 | 7/1991 |
| DE | 4206433 | 9/1993 |
| DE | 4303882 | 8/1994 |
| DE | 4339049 | 5/1995 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19848540 | 5/2000 |
| DE | 10045375 | 10/2002 |
| DE | 10 2004 02617 | 12/2005 |
| DE | 20 2007 00931 | 10/2007 |
| DE | 19738457 | 1/2009 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1159926 | 12/2001 |
| EP | 1366724 | 1/2006 |
| EP | 880220 | 6/2006 |
| EP | 1776929 | 4/2007 |
| EP | 1994904 | 11/2008 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 166452 | 1/1965 |
| SU | 401367 | 11/1974 |
| SU | 727201 | 4/1980 |
| WO | WO 00/36986 | 6/2000 |
| WO | WO 01/54604 | 8/2001 |
| WO | WO02/11634 | 2/2002 |
| WO | WO02/45589 | 6/2002 |
| WO | WO03/090635 | 11/2003 |
| WO | WO2004/032777 A1 | 4/2004 |
| WO | WO 2005/110264 | 11/2005 |
| WO | WO2006/050888 | 5/2006 |

OTHER PUBLICATIONS

Vallfors et al., "Automatically Controlled Bipolar Electrosoagulation-'COA-COMP'" Neurosurgical Review 7:2-3 (1984) pp. 187-190.

(56) References Cited

OTHER PUBLICATIONS

Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep., 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et at, "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.

(56) References Cited

OTHER PUBLICATIONS

Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et at, "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 10/406,690, filed Apr. 3, 2003, Michael S. Klicek.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 10/573,713, filed Mar. 28, 2006, Robert H. Wham.
U.S. Appl. No. 12/336,970, filed Dec. 17, 2008, Paul R. Sremcich.
U.S. Appl. No. 12/351,935, filed Jan. 12, 2009, Ronald J. Podhajsky.
U.S. Appl. No. 12/351,947, filed Jan. 12, 2009, Ronald J. Podhajsky.
U.S. Appl. No. 12/351,960, filed Jan. 12, 2009, Ronald J. Podhajsky.
U.S. Appl. No. 12/351,970, filed Jan. 12, 2009, Ronald J. Podhajsky.
U.S. Appl. No. 12/351,980, filed Jan. 12, 2009, Ronald J. Podhajsky.
U.S. Appl. No. 12/353,002, filed Jan. 13, 2009, Daniel A. Joseph.
U.S. Appl. No. 12/353,012, filed Jan. 13, 2009, Daniel A. Joseph.
U.S. Appl. No. 12/429,533, filed Apr. 24, 2009, David N. Heard.
U.S. Appl. No. 12/434,382, filed May 1, 2009, Thomas Rachlin.
U.S. Appl. No. 12/437,254, filed May 7, 2009, Duane E. Kerr.
U.S. Appl. No. 12/477,245, filed Jun. 3, 2009, Ronald J. Podhajsky.
U.S. Appl. No. 12/503,256, filed Jul. 15, 2009, Ryan C. Artale.
U.S. Appl. No. 12/534,308, filed Aug. 3, 2009, James A. Gilbert.
U.S. Appl. No. 12/535,869, filed Aug. 5, 2009, Arlan J. Reschke.
U.S. Appl. No. 12/540,190, filed Aug. 12, 2009, James A. Gilbert.
U.S. Appl. No. 12/543,831, filed Aug. 19, 2009, Arlan J. Reschke.
U.S. Appl. No. 12/548,031, filed Aug. 26, 2009, Peter M. Mueller.
U.S. Appl. No. 12/548,534, filed Aug. 27, 2009, Thomas J. Gerhardt.
U.S. Appl. No. 12/548,566, filed Aug. 27, 2009, John J. Kappus.
U.S. Appl. No. 12/549,563, filed Aug. 28, 2009, James A. Gilbert.
U.S. Appl. No. 12/551,944, filed Sep. 1, 2009, Sean T. Dycus.
U.S. Appl. No. 12/553,509, filed Sep. 3, 2009, Paul R. Romero.
U.S. Appl. No. 12/556,025, filed Sep. 9, 2009, Arlen J. Reschke.
U.S. Appl. No. 12/556,407, filed Sep. 9, 2009 Kim V. Brandt.
U.S. Appl. No. 12/556,427, filed Sep. 9, 2009, Peter Michael Mueller.
U.S. Appl. No. 12/556,796, filed Sep. 10, 2009, Jennifer S. Harper.
U.S. Appl. No. 12/556,770, filed Sep. 10, 2009 James A. Gilbert.
U.S. Appl. No. 12/562,281, filed Sep. 18, 2009, Patrick L. Dumbauld.
U.S. Appl. No. 12/565,281, filed Sep. 23, 2009, William J. Dickhans.
U.S. Appl. No. 12/566,173, filed Sep. 24, 2009, James A. Gilbert.
U.S. Appl. No. 12/566,233, filed Sep. 24, 2009, William N. Gregg.
U.S. Appl. No. 12/568,199, filed Sep. 28, 2009, Kim V. Brandt.
U.S. Appl. No. 12/568,282, filed Sep. 28, 2009, Kim V. Brandt.
U.S. Appl. No. 12/567,966, filed Sep. 28, 2009, Craig A. Keller.
U.S. Appl. No. 12/568,838, filed Sep. 29, 2009, Kenlyn S. Bonn.
U.S. Appl. No. 12/569,395, filed Sep. 29, 2009, Weng-Kai K. Lee.
U.S. Appl. No. 12/569,710, filed Sep. 29, 2009, Dylan R. Kingsley.
U.S. Appl. No. 12/574,001, filed Oct. 6, 2009, Duane E. Kerr.
U.S. Appl. No. 12/574,292, filed Oct. 6, 2009, Duane E. Kerr.
U.S. Appl. No. 12/576,380, filed Oct. 9, 2009, Wayne Siebrecht.
U.S. Appl. No. 12/597,213, filed Oct. 23, 2009, Ryan Artale.
U.S. Appl. No. 12/607,191, filed Oct. 28, 2009, William H. Nau Jr.
U.S. Appl. No. 12/613,876, filed Nov. 6, 2009, Craig A. Keller.
U.S. Appl. No. 12/619,100, filed Nov. 16, 2009, Jennifer S. Harper.
U.S. Appl. No. 12/619,234, filed Nov. 16, 2009, James A. Gilbert.
U.S. Appl. No. 12/639,210, filed Dec. 16, 2009, Jennifer S. Harper.
U.S. Appl. No. 12/665,081, filed Dec. 17, 2009, Timmy Floume.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/712,712, filed Feb. 25, 2010, Mani N. Prakash.
U.S. Appl. No. 12/713,956, filed Feb. 26, 2010, Robert B. Smith.
U.S. Appl. No. 12/715,212, filed Mar. 1, 2010, Robert J. Behnke II.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/754,420, filed Apr. 5, 2010, Robert H. Wham.
U.S. Appl. No. 12/754,429, filed Apr. 5, 2010, Robert H. Wham.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Homer.
U.S. Appl. No. 12/769,444, filed Apr. 28, 2010, Glenn A. Homer.
U.S. Appl. No. 12/770,369, filed Apr. 29, 2010, Glenn A. Homer.
U.S. Appl. No. 12/770,380, filed Apr. 29, 2010, Glenn A. Homer.
U.S. Appl. No. 12/770,387, filed Apr. 29, 2010, Glenn A. Homer.
U.S. Appl. No. 12/772,345, filed May 3, 2010, Darren Odom.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/775,553, filed May 7, 2010, Matthew Chowaniec.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Homer.
U.S. Appl. No. 12/792,051, filed Jun. 2, 2010, David M. Garrison.
U.S. Appl. No. 12/792,068, filed Jun. 2, 2010, Glenn A. Homer.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/833,270, filed Jul. 9, 2010, David Hixson.
U.S. Appl. No. 12/843,384, filed Jul. 26, 2010, David M. Garrison.
U.S. Appl. No. 12/846,602, filed Jul. 29, 2010, Timothy J. Bahney.
U.S. Appl. No. 12/853,896, filed Aug. 10, 2010, William H. Nau Jr.
U.S. Appl. No. 12/859,896, filed Aug. 20, 2010, Peter Michael Mueller.
U.S. Appl. No. 12/859,985, filed Aug. 20, 2010 David A. Schechter.
U.S. Appl. No. 12/861,198, filed Aug. 23, 2010, James A. Gilbert.
U.S. Appl. No. 12/861,209, filed Aug. 23, 2010, William H. Nau Jr.
U.S. Appl. No. 12/876,662, filed Sep. 7, 2010, Kate Lawes.
U.S. Appl. No. 12/876,668, filed Sep. 7, 2010, Sara E. Anderson.
U.S. Appl. No. 12/876,680, filed Sep. 7, 2010, Peter Michael Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/879,505, filed Sep. 10, 2010, David A. Schechter.
U.S. Appl. No. 12/882,304, filed Sep. 15, 2010, Kristin D. Johnson.
U.S. Appl. No. 12/895,020, filed Sep. 30, 2010, Jeffrey M. Roy.
U.S. Appl. No. 12/896,100, filed Oct. 1, 2010, Ryan C. Artale.
U.S. Appl. No. 12/897,346, filed Oct. 4, 2010, Ryan C. Artale.
U.S. Appl. No. 09/387,883, filed Sep. 1, 1999.
U.S. Appl. No. 09/591,328, filed Jun. 9, 2000.
U.S. Appl. No. 10/406,690, filed Apr. 3, 2003.
U.S. Appl. No. 10/761,524, filed Jan. 21, 2004.
U.S. Appl. No. 11/242,458, filed Oct. 3, 2005.
U.S. Appl. No. 10/573,713, filed Mar. 28, 2006.
U.S. Appl. No. 12/336,970, filed Dec. 17, 2008.
U.S. Appl. No. 12/351,935, filed Jan. 12, 2009.
U.S. Appl. No. 12/351,947, filed, Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/429,533, filed Apr. 24, 2009.

(56) References Cited

OTHER PUBLICATIONS

U.S. Appl. No. 12/434,382, filed May 1, 2009.
U.S. Appl. No. 12/437,254, filed May 7, 2009.
U.S. Appl. No. 12/477,245, filed Jun. 3, 2009.
U.S. Appl. No. 12/503,256, filed Jul. 15, 2009.
U.S. Appl. No. 12/534,308, filed Aug. 3, 2009.
U.S. Appl. No. 12/535,869, filed Aug. 5, 2009.
U.S. Appl. No. 12/540,190, filed Aug. 12, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/549,563, filed Aug. 28, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/556,770, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/566,173, filed Sep. 24, 2009.
U.S. Appl. No. 12/566,233, filed Sep. 24, 2009.
U.S. Appl. No. 12/568,199, filed Sep. 28, 2009.
U.S. Appl. No. 12/568,282, filed Sep. 28, 2009.
U.S. Appl. No. 12/567,966, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/613,876, filed Nov. 6, 2009.
U.S. Appl. No. 12/619,100, filed Nov. 16, 2009.
U.S. Appl. No. 12/619,234, filed Nov. 16, 2009.
U.S. Appl. No. 12/639,210, filed Dec. 16, 2009.
U.S. Appl. No. 12/665,081, filed Dec. 17, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/712,712, filed Feb. 25, 2010.
U.S. Appl. No. 12/713,956, filed Feb. 26, 2010.
U.S. Appl. No. 12/715,212, filed Mar. 1, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/754,420, filed Apr. 5, 2010.
U.S. Appl. No. 12/754,429, filed Apr. 5, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/772,345, filed May 3, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/833,270, filed Jul. 9, 2010.
U.S. Appl. No. 12/843,384, filed Jul. 26, 2010.
U.S. Appl. No. 12/845,203, filed Jul. 28, 2010.
U.S. Appl. No. 12/846,602, filed Jul. 29, 2010.
U.S. Appl. No. 12/853,896, filed Aug. 10, 2010.
U.S. Appl. No. 12/859,896, filed Aug. 20, 2010.
U.S. Appl. No. 12/859,985, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,662, filed Sep. 7, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/879,505, filed Sep. 10, 2010.
U.S. Appl. No. 12/882,304, filed Sep. 15, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, DATED: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.

(56) References Cited

OTHER PUBLICATIONS

International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP 08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended-EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended-EP 07 009029.5 dated Jul. 20, 2007.
Int'l Search Report EP 07 009321.6 dated Aug. 28, 2007.
Int'l Search Report EP 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.

(56) References Cited

OTHER PUBLICATIONS

Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11006233.8 dated Jan. 26, 2012.

* cited by examiner

LOCAL OPTIMIZATION OF ELECTRODE CURRENT DENSITIES

BACKGROUND

1. Technical Field

The following disclosure relates to an apparatus, system, and method for performing an electrosurgical procedure and, more particularly, to local optimization of electrode current densities utilizing electrode geometries.

2. Description of Related Art

It is well known in the art that electrosurgical generators are employed by surgeons in conjunction with electrosurgical instruments to perform a variety of electrosurgical surgical procedures (e.g., tonsillectomy, adenoidectomy, etc.). An electrosurgical generator generates and modulates electrosurgical energy which, in turn, is applied to the tissue by an electrosurgical instrument. Electrosurgical instruments may be either monopolar or bipolar and may be configured for open or endoscopic procedures.

Electrosurgical instruments may be implemented to ablate, seal, cauterize, coagulate, and/or desiccate tissue and, if needed, cut and/or section tissue. Typically, cutting and/or sectioning tissue is performed with a knife blade movable within a longitudinal slot located on or within one or more seal plates associated with one or more jaw members configured to receive a knife blade, or portion thereof. The longitudinal slot is normally located on or within the seal plate within a treatment zone (e.g., seal and/or coagulation zone) associated therewith. Consequently, the knife blade cuts and/or sections through the seal and/or coagulation zone during longitudinal translation of the knife blade through the longitudinal slot. In some instances, it is not desirable to cut through the zone of sealed or coagulated tissue, but rather to the left or right of the zone of sealed or coagulated tissue such as, for example, during a tonsillectomy and/or adenoidectomy procedure.

SUMMARY

According to an embodiment of the present disclosure, an end effector assembly for use with a bipolar forceps includes a pair of opposing first and second jaw members at least one of which being movable relative to the other to grasp tissue therebetween. Each jaw member includes a pair of spaced apart, electrically conductive tissue sealing surfaces. Each tissue sealing surface is adapted to connect to a source of electrosurgical energy to conduct electrosurgical energy through tissue held therebetween to effect a tissue seal. The end effector assembly also includes an insulator disposed between each pair of electrically conductive sealing surfaces and an electrically conductive cutting element disposed within each insulator and defining a geometrical configuration including a plurality of peaks having a period that is a multiple of an operating frequency of the electrosurgical energy. The cutting elements are adapted to connect to the source of electrosurgical energy to conduct electrosurgical energy through tissue held therebetween to effect a tissue cut.

According to another embodiment of the present disclosure, an end effector assembly for use with a bipolar forceps includes a pair of opposing first and second jaw members at least one of which being movable relative to the other from a first position wherein the jaw members are disposed in spaced relation to one another to a second position wherein the jaw members cooperate to grasp tissue therebetween. Each jaw member includes a pair of spaced apart, electrically conductive tissue sealing surfaces extending along a length thereof. Each tissue sealing surface is adapted to connect to a source of electrosurgical energy to conduct electrosurgical energy through tissue held therebetween to effect a tissue seal. The end effector assembly also includes an insulator disposed between each pair of electrically conductive sealing surfaces and an electrically conductive cutting element disposed within the insulator of the first jaw member and in general vertical registration with an electrically conductive cutting element disposed within the insulator of the second jaw member. Each of the electrically conductive cutting elements includes a plurality of peaks offset from a plurality of peaks of the other cutting element. The number of peaks of at least one of the cutting elements is a function of a wavelength of an operating frequency of the electrosurgical energy. The cutting elements are adapted to connect to the source of electrosurgical energy to conduct electrosurgical energy through tissue held therebetween to effect a tissue cut. The cutting elements are inactive during tissue sealing and the pair of spaced apart electrically conductive sealing surfaces on the first jaw member are energized to a different potential from the corresponding pair of spaced apart electrically conductive sealing surfaces on the second jaw member such that electrosurgical energy can be transferred through the tissue to effect a tissue seal.

According to another embodiment of the present disclosure, a method of manufacturing an electrically conductive cutting element adapted to be coupled to an end effector assembly for effecting a tissue cut includes the steps of providing an electrically conductive electrode having a predetermined length and calculating a number of peaks along the predetermined length and a period based on a repetition of the peaks. The number of peaks is a function of an operating frequency of an energy source adapted to supply electrosurgical energy to the electrically conductive cutting element.

BRIEF DESCRIPTION OF THE DRAWINGS

Various embodiments of the present disclosure are described hereinbelow with references to the drawings, wherein.

DETAILED DESCRIPTION

Figure 1A:
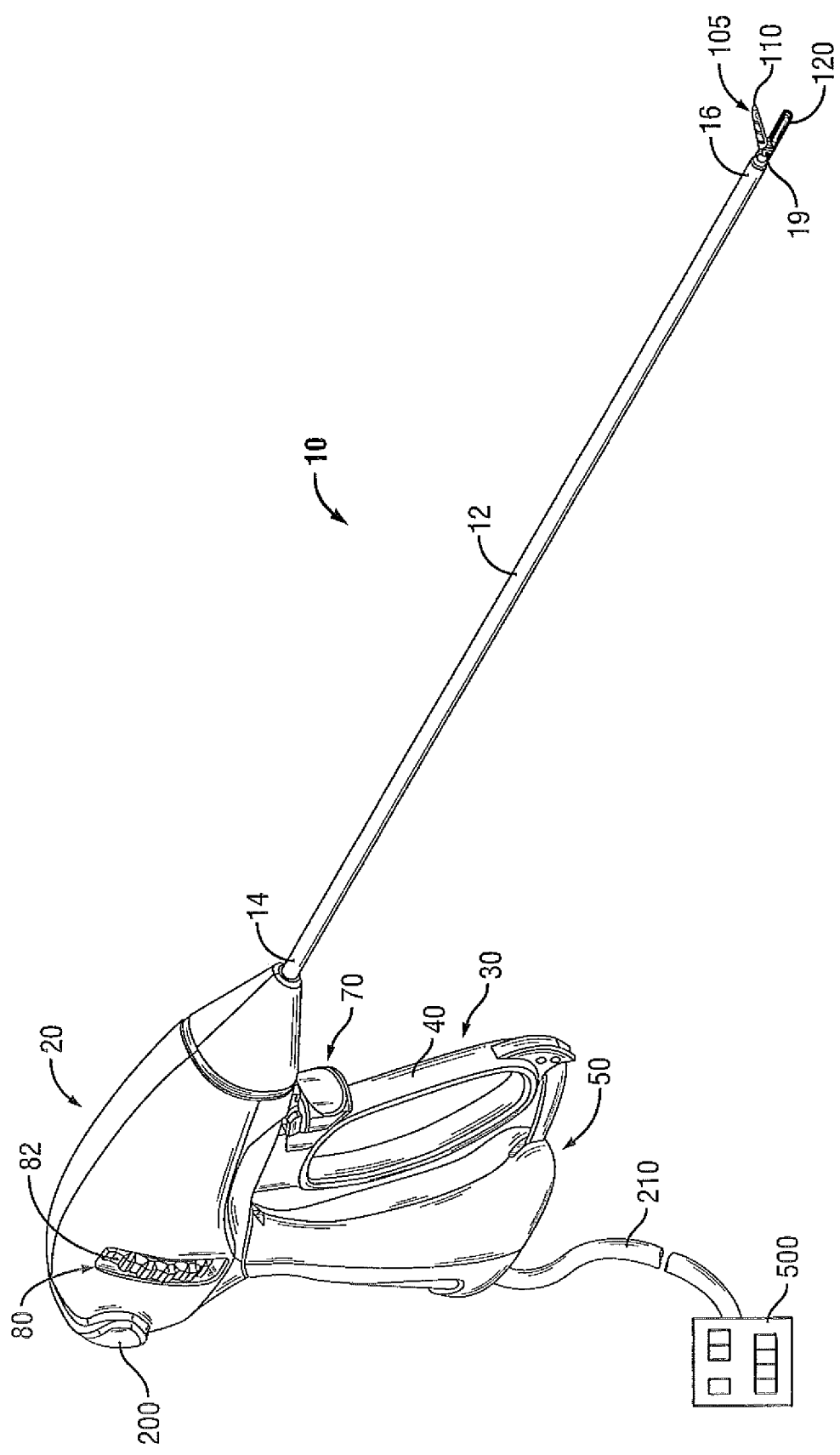
FIG. 1A is a right, perspective view of an endoscopic bipolar forceps in accordance with an embodiment of the present disclosure.

For the purposes herein, vessel/tissue cutting or vessel/tissue division is believed to occur when heating of the vessel/tissue leads to expansion of intracellular and/or extra-cellular fluid, which may be accompanied by cellular vaporization, desiccation, fragmentation, collapse and/or shrinkage along a so-called "cut zone" in the vessel/tissue. By focusing the electrosurgical energy and heating in the cut zone, the cellular reactions are localized creating a fissure. Localization is achieved by regulating the vessel/tissue condition and energy delivery, which may be controlled by utilizing one or more of the various geometrical electrode configurations described herein. The cut process may also be controlled by utilizing a generator and feedback algorithm (and one or more of the hereindescribed geometrical configurations of the electrode assemblies) that increases the localization and maximizes the so-called "cutting effect".

In general, the below-described factors contribute and/or enhance vessel/tissue division using electrosurgical energy. Each of the factors described below may be employed individually or in any combination to achieve a desired cutting effect. For the purposes herein, the term "cut effect" or "cutting effect" refers to the actual division of tissue by one or more of the electrical or electromechanical methods or mechanisms described below. The term "cutting zone" or "cut zone" refers to the region of vessel/tissue where cutting will take place. The term "cutting process" refers to steps that are implemented before, during, and/or after vessel/tissue division that tend to influence the vessel/tissue as part of achieving the cut effect.

For the purposes herein, the terms "tissue" and "vessel" may be used interchangeably since it is believed that the present disclosure may be employed to seal and cut tissue or seal and cut vessels utilizing the same principles described in the present disclosure.

By way of example and without limitation, factors that either alone or in combination play an important role in dividing tissue include: (1) localizing or focusing electrosurgical energy in the cut zone during the cutting process while minimizing energy effects to surrounding tissues; (2) focusing the current density in the cut zone during the cutting process; (3) creating an area of increased temperature in the cut zone during the cutting process (e.g., heating that occurs within the tissue or heating the tissue directly with a heat source); and (4) pulsing the energy delivery to influence the tissue in or around the cut zone.

Electrode assemblies described herein utilize various geometrical configurations of electrodes, cutting elements, insulators, partially conductive materials, and semiconductors to produce or enhance the cutting effect. In addition, by controlling or regulating the electrosurgical energy from the generator in any of the ways described above, tissue cutting may be initiated, enhanced, or facilitated within the tissue cutting zone.

For example, the geometrical configuration of the electrodes may be configured to produce a so-called "cut effect" that is directly related to the current density applied to a point in the tissue. The geometry of the electrodes may be configured such that the surface area ratios between the electrical poles focus electrical energy at the tissue. Moreover, optimization of the "cut effect" may be achieved by configuring the geometry of bipolar-type electrodes to include a specific number of peaks (see FIGS. 4A, 4B, and 4C) as a function of the operating frequency (e.g., the fundamental frequency) of the energy source used to produce the "cut effect". More specifically, bipolar-type electrodes having peaks repeating at a particular period T (see FIG. 4A) and that period T is a multiple of the operating frequency of the energy being applied to tissue to produce the "cut effect", the current density between the electrodes will be maximized, thereby optimizing the "cut effect". The present disclosure provides for various electrode geometries configured in accordance with the operating frequency of the output energy and a method for calculating such geometric configurations as a function of the operating frequency of energy output for purposes of optimizing the "cut effect".

Figure 1B:
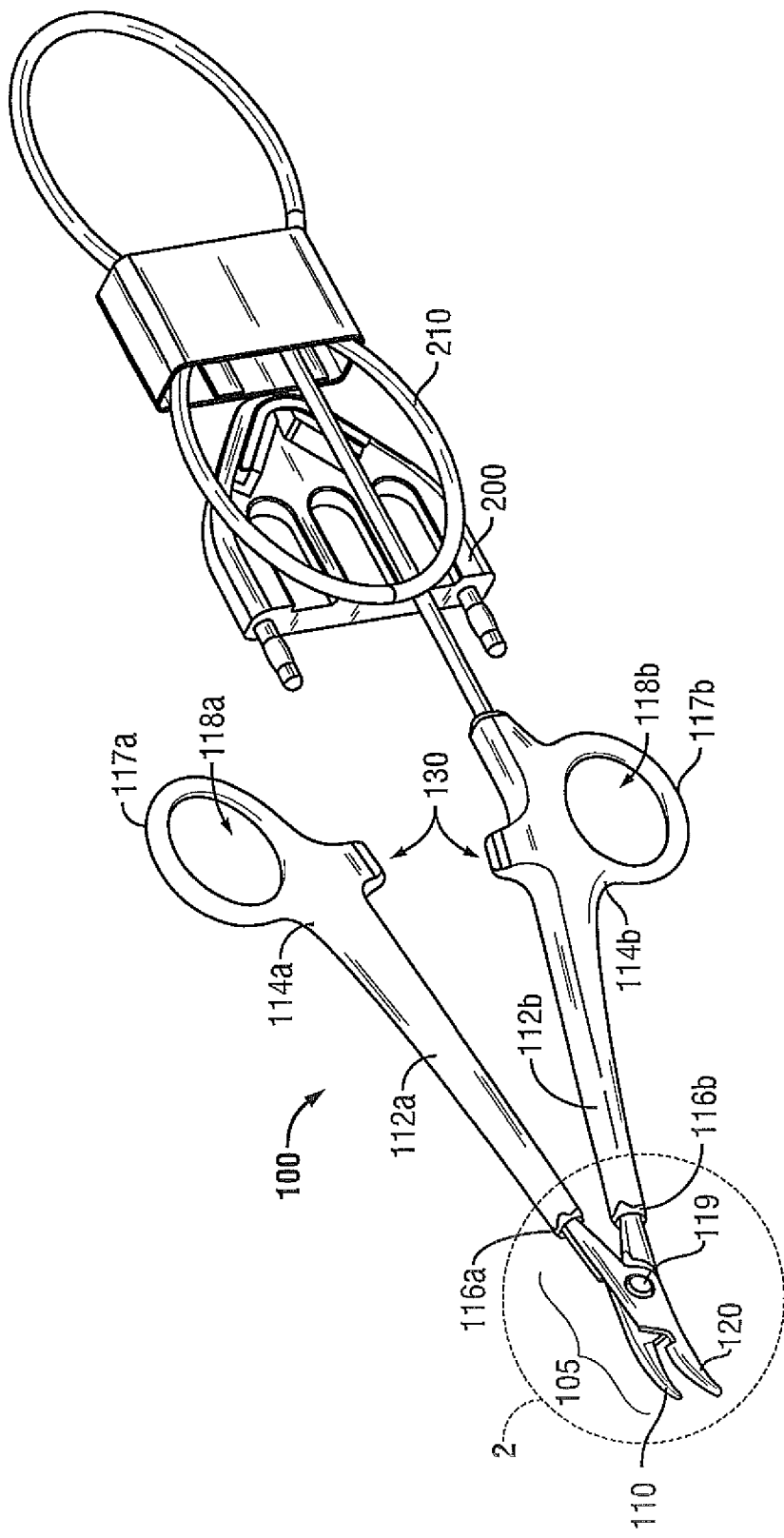
FIG. 1B is a left, perspective view of an open bipolar forceps in accordance with an embodiment of the present disclosure.

Referring now to FIGS. 1A and 1B, FIG. 1A depicts a bipolar forceps 10 for use in connection with endoscopic surgical procedures and FIG. 1B depicts an open forceps 100 for use in connection with traditional open surgical procedures. For the purposes herein, either an endoscopic instrument or an open instrument may be utilized with the electrode assembly described herein. Different electrical and mechanical connections and considerations apply to each particular type of instrument, however, the novel aspects with respect to the electrode assembly and its operating characteristics remain generally consistent with respect to both the open or endoscopic designs.

FIG. 1A shows a bipolar forceps 10 for use with various endoscopic surgical procedures and generally includes a housing 20, a handle assembly 30, a rotating assembly 80, a switch assembly 70, and an electrode assembly 105 having opposing jaw members 110 and 120 that mutually cooperate to grasp, seal, and divide tubular vessels and vascular tissue. More particularly, forceps 10 includes a shaft 12 which has a distal end 16 dimensioned to mechanically engage the electrode assembly 105 and a proximal end 14 that mechanically engages the housing 20. The shaft 12 includes one or more mechanically engaging components that are designed to securely receive and engage the electrode assembly 105 such that the jaw members 110 and 120 are pivotable about a pivot pin 19 relative to one another to engage and grasp tissue therebetween.

The proximal end 14 of shaft 12 mechanically engages the rotating assembly 80 (not shown) to facilitate rotation of the electrode assembly 105. In the drawings and in the descriptions that follow, the term "proximal", as is traditional, will refer to the end of the forceps 10 that is closer to the user, while the term "distal" will refer to the end that is farther from the user. Details relating to the mechanically cooperating components of the shaft 12 and the rotating assembly 80 are described in commonly-owned U.S. Pat. No. 7,156,846.

Handle assembly 30 includes a fixed handle 50 and a movable handle 40. Fixed handle 50 is integrally associated with housing 20 and, handle 40 is movable relative to fixed handle 50 to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. Switch assembly 70 is configured to selectively provide electrical energy to the electrode assembly 105.

Referring now to FIG. 1B, an open forceps 100 includes a pair of elongated shaft portions 112a and 112b each having a proximal end 114a and 114b, respectively, and a distal end 116a and 116b, respectively. The forceps 100 includes jaw members 120 and 110 which attach to distal ends 116a and 116b of shafts 112a and 112b, respectively. The jaw members 110 and 120 are connected about pivot pin 119 such that jaw members 110 and 120 pivot relative to one another from the first to second positions for treating tissue. The electrode assembly 105 is connected to opposing jaw members 110 and 120 and may include electrical connections through or around the pivot pin 119.

Each shaft 112a and 112b includes a handle 117a and 117b disposed at the proximal end 114a and 114b thereof which each define a finger hole 118a and 118b, respectively, therethrough for receiving a finger of the user. Finger holes 118a and 118b facilitate movement of the shafts 112a and 112b relative to one another that, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween.

A ratchet 130 is included for selectively locking the jaw members 110 and 120 relative to one another at various positions during pivoting.

As best seen in FIG. 1B, forceps 100 also includes an electrical interface or plug 200 that connects the forceps 100 to a source of electrosurgical energy, e.g., electrosurgical generator 500 (FIG. 1A). An electrical cable 210 extends from the plug 200 and securely connects the cable 210 to the forceps 100. Cable 210 is internally divided within the shaft 112b to transmit electrosurgical energy through various electrical feed paths to the electrode assembly 105.

One of the shafts, e.g., 112b, includes a proximal shaft connector/flange 121 that is configured to connect the forceps 100 to a source of electrosurgical energy (e.g., electrosurgical generator 500). More particularly, flange 121 mechanically secures electrosurgical cable 210 to the forceps 100 such that the user may selectively apply electrosurgical energy as needed.

Figure 2:
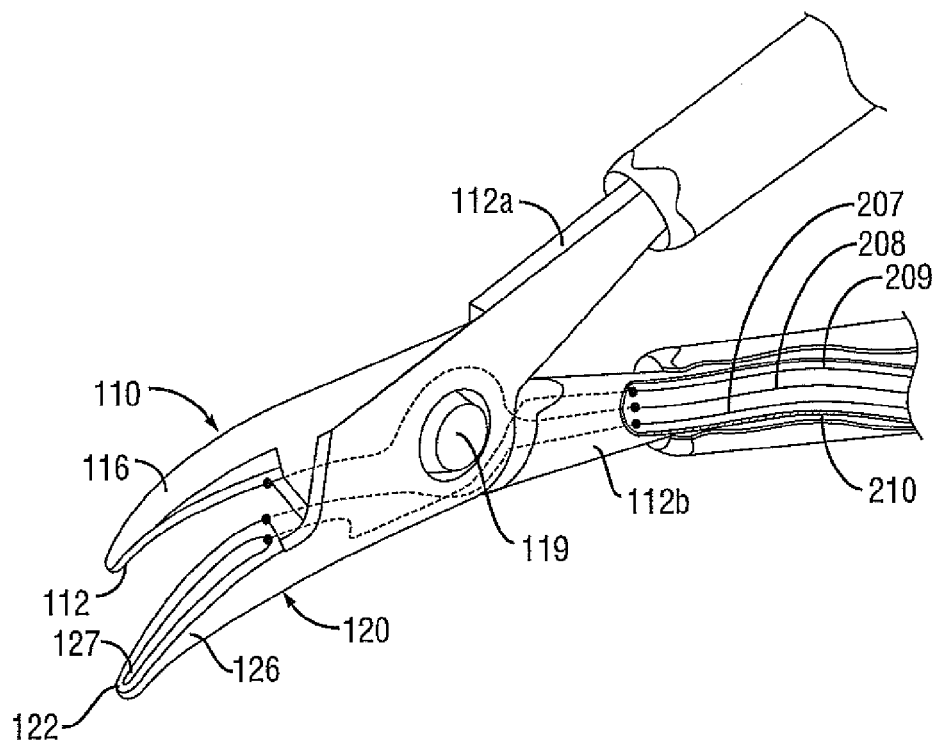
FIG. 2 is an enlarged view of the area of detail of FIG. 1B.

As best shown in the schematic illustration of FIG. 2, the jaw members 110 and 120 of both the endoscopic version of FIG. 1A and the open version of FIG. 1B are generally symmetrical and include similar component features that cooperate to permit facile rotation about pivot 19, 119 to effect the grasping and sealing of tissue. Each jaw member 110 and 120 includes an electrically conductive tissue contacting surface 112 and 122, respectively, that cooperate to engage the tissue during sealing and cutting. At least one of the jaw members, e.g., jaw member 120, includes an electrically energizable cutting element 127 disposed therein, explained in detail below. Together and as shown in the various figure drawings described hereafter, the electrode assembly 105 includes the combination of the sealing electrodes 112 and 122 and the cutting element(s) 127.

The various electrical connections of the electrode assembly 105 are configured to provide electrical continuity to the tissue contacting surfaces 110 and 120 and the cutting element(s) 127 through the electrode assembly 105. For example, cable lead 210 may be configured to include three different leads, namely, leads 207, 208 and 209 that carry different electrical potentials. The cable leads 207, 208 and 209 are fed through shaft 112b and connect to various electrical connectors (not shown) disposed within the proximal end of the jaw member 110 which ultimately connect to the electrically conductive sealing surfaces 112 and 122 and cuffing element(s) 127.

The various electrical connections from lead 210 are dielectrically insulated from one another to allow selective and independent activation of either the tissue contacting surfaces 112 and 122 or the cutting element 127. Alternatively, the electrode assembly 105 may include a single connector that includes an internal switch (not shown) to allow selective and independent activation of the tissue contacting surfaces 112, 122 and the cutting element 127.

Figure 3:
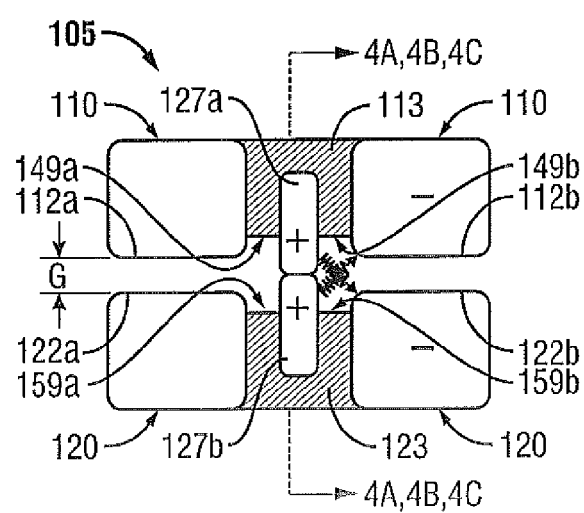
FIG. 3 is an enlarged, schematic end view of an electrode assembly according to an embodiment of the present disclosure.

As best seen in FIG. 3, an embodiment of the electrode assembly 105 is shown that is configured to effectively seal and cut tissue disposed between the sealing surfaces 112 and 122 and the cutting elements 127 of the opposing jaw members 110 and 120, respectively. More particularly and with respect to FIGS. 2 and 3, jaw members 110 and 120 include conductive tissue contacting surfaces 112 and 122, respectively, disposed along substantially the entire longitudinal length thereof (e.g., extending substantially from the proximal to distal end of the respective jaw member 110 and 120). In embodiments, tissue contacting surfaces 112 and 122 may be attached to the jaw members 110, 120 by stamping, by overmolding, by casting, by overmolding a casting, by coating a casting, by overmolding a stamped electrically conductive sealing plate, and/or by overmolding a metal injection molded seal plate.

With respect to FIG. 3, jaw members 110 and 120 both include an insulator or insulative material 113 and 123, respectively, disposed between each pair of electrically conductive sealing surfaces on each jaw member 110 and 120, i.e., between pairs 112a and 112b and between pairs 122a and 122b. Each insulator 113 and 123 is generally centered between its respective tissue contacting surface 112a, 112b and 122a, 122b along substantially the entire length of the respective jaw member 110 and 120 such that the two insulators 113 and 123 generally oppose one another.

At least one jaw member 110 and/or 120 includes an electrically conductive cutting element 127 disposed substantially within or disposed on the insulator 113, 123. As described in detail below, the cutting element 127 (in many of the embodiments described hereinafter) plays a dual role during the sealing and cutting processes, namely: 1) to provide the necessary gap distance between conductive surfaces 112a, 112b and 122a, 122b during the sealing process; and 2) to electrically energize the tissue along the previously formed tissue seal to cut the tissue along the seal. With respect to FIG. 3, the cutting elements 127a, 127b are electrically conductive, however, one or both of the cutting elements 127a, 127b may be made from an insulative material with a conductive coating disposed thereon or one (or both) of the cutting elements 127a, 127b may be non-conductive. In some embodiments, the distance between the cutting element(s) 127a and the opposing cutting element 127b (or the opposing return electrode in some cases) is within the range of about 0.008 inches to about 0.015 inches to optimize the cutting effect.

The general characteristics of the jaw members 110 and 120 and the electrode assembly 105 will initially be described with respect to FIG. 3 while the changes to the other embodiments disclosed herein will become apparent during the description of each individual embodiment. Moreover, FIG. 3 shows an electrical configuration and polarity during the cutting phase only. During the so called "sealing phase", the jaw members 110 and 120 are closed about tissue and the cutting elements 127a and 127b form the requisite gap between the opposing sealing surfaces 112a, 122a and 112b, 122b. During activation of the sealing phase, the cutting elements 127a and 127b are not necessarily energized such that the majority of the current is concentrated between opposing sealing surfaces, 112a and 122a and 112b and 122b to effectively seal the tissue. In embodiments, stop members (not shown) may be employed to regulate the gap distance between the sealing surfaces in lieu of the cutting elements 127a and 127b. The stop members may be disposed on the sealing surfaces 112a, 122a and 112b, 122b, adjacent the sealing surfaces 112a, 122a and 112b, 122b or on the insulator(s) 113, 123.

In some embodiments, the cutting elements 127a and 127b are configured to extend from their respective insulators 113 and 123, respectively, and extend beyond the tissue contacting surfaces 112a, 112b and 122a, 122b such that the cutting elements 127a and 127b act as stop members (i.e., create a gap distance "G" (See FIG. 3) between opposing conductive sealing surfaces 112a, 122a and 112b, 122b) that as mentioned above, promotes accurate, consistent, and effective tissue sealing. The cutting elements 127a and 127b also prevent the opposing tissue contacting surfaces 112a, 122a and 112b, 122b from touching to eliminate the chances of the forceps 10, 100 shorting during the sealing process.

With respect to FIG. 3, the conductive cutting elements 127a and 127b are oriented in opposing, vertical registration within respective insulators 113 and 123 of jaw members 110 and 120. In some embodiments, the cutting elements 127a and 127b are substantially dull so as to not inhibit the sealing process (i.e., premature cutting) during the sealing phase of the electrosurgical activation. In other words, the surgeon is free to manipulate, grasp and clamp the tissue for sealing purposes without the cutting elements 127a and 127b mechanically cutting into the tissue. Moreover, in this instance, tissue cutting can only be achieved through either: 1) a combination of mechanically clamping the tissue between the cutting elements 127a and 127b and applying electrosurgical energy from the cutting elements 127a and 127b, through the tissue and to the return electrodes, i.e., the electrically conductive tissue contacting surfaces 112b and 122b as shown in FIG. 3; or 2) applying electrosurgical energy from the cutting elements 127a and 127b through the tissue and to the return tissue contacting surfaces 112b and 122b.

In some embodiments, the geometrical configuration of the cutting elements 127a and 127b may, at least in part, determine the overall effectiveness of the tissue cut. Certain geometries of the cutting elements 127a and 127b may create higher areas of current density than other geometries. Moreover, the spacing of the return electrodes 112b and 122b to these current density affects the electrical fields through the tissue. Therefore, by configuring the cutting elements 127a and 127b and the respective insulators 113 and 123 within close proximity to one another, the current density remains high which is ideal for cutting and the instrument will not short due to accidental contact between conductive surfaces. The relative size of the cutting elements 127a and 127b and/or the size of the insulator 113 and 123 may be selectively altered depending upon a particular or desired purpose to produce a particular surgical effect.

Turning now to the embodiments of the electrode assembly 105 as disclosed herein, FIG. 3 as mentioned above includes first and second jaw members 110 and 120 having an electrode assembly 105 disposed thereon. More particularly, the electrode assembly 105 includes first electrically conductive sealing surfaces 112a and 112b each disposed in opposing registration with second electrically conductive sealing surfaces 122a and 122b on jaw members 110 and 120, respectively. Insulator 113 electrically isolates sealing surfaces 112a and 112b from one another allowing selective independent activation of the sealing surfaces 112a and 112b. Insulator 123 separates sealing surfaces 122a and 122b from one another in a similar manner thereby allowing selective activation of sealing surfaces 122a and 122b.

Each insulator 113 and 123 is set back a predetermined distance between the sealing surfaces 112a, 112b and 122a, 122b to define a recess 149a, 149b and 159a, 159b, respectively, that as mentioned above, affects the overall current densities between the electrically activated surfaces during both the sealing and cutting phases. Cutting element 127a is disposed within and/or deposited on insulator 113 and extends inwardly therefrom to extend beyond the sealing surfaces 112a, 112b by a predetermined distance.

During sealing, the opposing sealing surfaces 112a, 122a and 112b, 122b are activated to seal the tissue disposed therebetween to create two tissue seals on either side of the insulators 113 and 123. During the cutting phase, the cutting elements 127a and 127b are energized with a first electrical potential "+" and the right opposing sealing surfaces 112b and 122b are energized with a second electrical potential "−". This creates a concentrated electrical path between the potentials "+" and "−" through the tissue to cut the tissue between the previously formed tissue seals. Once the tissue is cut, the jaw members 110 and 120 are opened to release the two tissue halves.

Figure 4A:
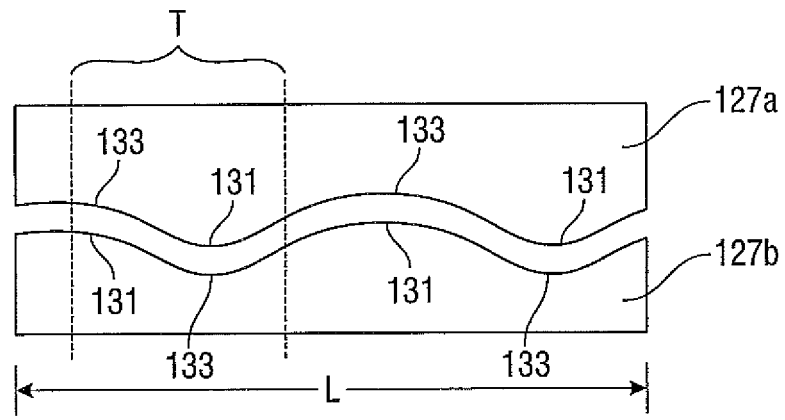
FIGS. 4A-4C are cross-sectional views taken along section line 4A, 4B, 4C-4A, 4B, 4C of FIG. 3 illustrating various geometric configurations of cutting elements according to various embodiments of the present disclosure.
Figure 4B:
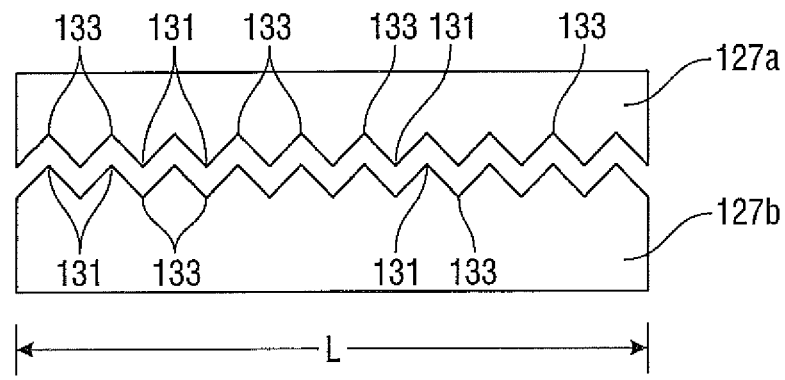
Figure 4C:
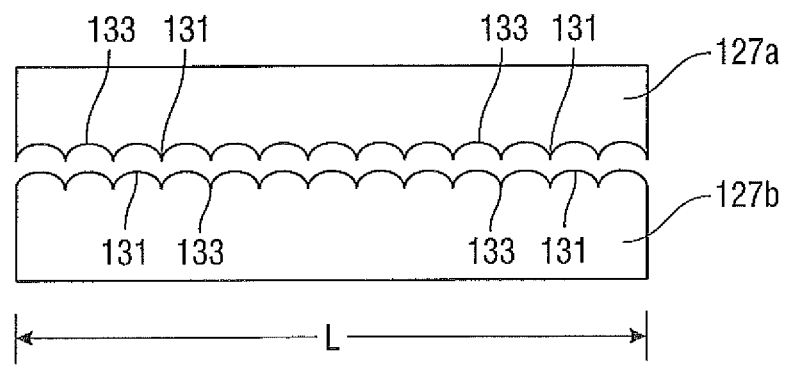

With reference to FIGS. 4A, 4B, and 4C, to maximize the current density between cutting elements 127a and 127b and, thereby optimize the "cutting effect", the geometry of the cutting elements 127a and 127b may be configured to include a plurality of peaks 131 separated by valleys 133 interposed therebetween to define waveforms having a period T (illustrated, for example, in FIG. 4A). In the illustrated embodiments of FIGS. 4A, 413, and 4C, the waveforms defined by cutting elements 127a, 127b are off-set from one another such that the peaks 131 of cutting element 127a complement the valleys 133 of cutting element 127b and vice-versa. The various peak 131 and valley 133 configurations depicted by FIGS. 4A, 4B, and 4C are intended to illustrate the concept that the period T of the waveforms defined by cutting element 127a and/or 127b is configured as a function of the operating frequency of the output energy from the energy source (e.g., generator 500) to maximize the current density between cutting elements 127a and 127b, thereby optimizing the "cut effect". The geometric configurations depicted by FIGS. 4A, 4B, and 4C are illustrative only in that any suitable geometric shape of peaks 131 and/or valleys 133 may be used to maximize current density between cutting elements 127a and 127b in the manner described hereinabove and hereinafter.

The relationship between the operating frequency of the energy source and the geometric configuration of the cutting element(s) 127a and/or 127b is illustrated by the following set of equations:

$$\lambda = f/v; \quad (1)$$

wherein $\lambda$ is the wavelength of the waveform defined by cutting element(s) 127a and/or 127b; f is the operating frequency (or fundamental frequency) of the output energy of the energy source (e.g., generator 500); and v is the velocity of the output energy.

Equation (1), in turn, is utilized to yield equation $$d = \lambda/x; \quad (2)$$

wherein d is a distance between any two points along the waveform defined by cutting element(s) 127a and/or 127b that may be used to define the period T of the waveform; and x is the number of peaks 131 along the waveform.

Equations (1) and (2), in turn, are utilized to yield equation $$d*x = f/v; \quad (3)$$

Equations (1) and (3), in turn, are utilized to yield equation $$d = \lambda/x; \quad (4)$$

wherein the number x of peaks 131 can be varied as necessary to yield the appropriate number of peaks 131 for a given length L of cutting element(s) 127a and/or 127b.

Utilizing equation (4), the current density between cutting elements 127a and 127b may be maximized by configuring each cutting element 127a and/or 127b to include the appropriate number x of peaks 131 for a given length L of cutting element 127a and/or 127b as a function of the wavelength $\lambda$ of the operating frequency of the energy source (e.g., generator 500) used to produce the "cut effect". In this manner, the "cut effect" produced by application of energy to tissue via cutting element(s) 127a and/or 127b is optimized.

When manufacturing cutting element(s) 127a and/or 127b, the "cut effect" may be optimized by using equation (4) to calculate the appropriate number of peaks x for a given length L of cutting element(s) 127a and/or 127b as a function of the operating frequency f of the energy source associated with forceps 10, 100. Conversely, the "cut effect" may be optimized by using equation (4) to calculate the appropriate operating frequency f as a function of the geometric configuration of cutting element(s) 127a and/or 127b (e.g., the number of peaks x for a given length L) and adjusting (e.g., discretely) the operating frequency of the energy source (e.g., generator 500) accordingly. That is, for example, a suitable control mechanism (not shown) may be disposed on the generator 500 to allow a user to selectively adjust the operating frequency of the generator 500 in accordance with the geometric configuration of a cutting element and/or electrode of an instrument connected to the generator 500 for purposes of sealing and/or cutting tissue utilizing the energy output of the generator 500.

In some embodiments, the current density and/or current concentration around the cutting elements 127a and 127b is based upon the particular geometrical configuration of the cutting elements 127a and 127b and the cutting elements' 127a and 127b proximity to the return electrodes, i.e., tissue contacting surfaces 112b and 122b.

In addition, the cutting element(s) 127a (and/or 127b) may be independently activated by the surgeon or automatically activated by the generator once sealing is complete. A safety algorithm may be employed to assure that an accurate and complete tissue seal is formed before cutting. An audible or visual indicator (not shown) may be employed to assure the surgeon that an accurate seal has been formed and the surgeon may be required to activate a trigger (or deactivate a safety) before cutting. For example, a smart sensor or feedback algorithm (not shown) may be employed to determine seal quality prior to cutting. The smart sensor or feedback loop may also be configured to automatically switch electrosurgical energy to the cutting element(s) 127a (and/or 127b) once the smart sensor determines that the tissue is properly sealed. In embodiments, the electrical configuration of the electrically conductive sealing surfaces 112a, 112b and 122a, 122b may be automatically or manually altered during the sealing and cutting processes to effect accurate and consistent tissue sealing and cutting.

The various geometrical configurations and electrical arrangements of the aforementioned electrode assemblies allow the surgeon to initially activate the two opposing electrically conductive tissue contacting surfaces and seal the tissue and, subsequently, selectively and independently activate the cutting element and one or more tissue contacting surfaces to cut the tissue utilizing the various above-described and shown electrode assembly configurations. Hence, the tissue is initially sealed and thereafter cut without re-grasping the tissue.

However, the cutting element and one or more tissue contacting surfaces may also be activated to simply cut tissue/vessels without initially sealing. For example, the jaw members may be positioned about tissue and the cutting element may be selectively activated to separate or simply coagulate tissue. This type of alternative embodiment may be particularly useful during certain endoscopic procedures wherein an electrosurgical pencil is typically introduced to coagulate and/or dissect tissue during the operating procedure.

A switch (e.g., switch assembly 70 shown in FIG. 1A) may be employed to allow the surgeon to selectively activate one or more tissue contacting surfaces or the cutting element independently of one another. This allows the surgeon to initially seal tissue and then activate the cutting element by simply actuating the switch.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An end effector assembly for use with a bipolar forceps, the end effector assembly comprising:
   a pair of opposing first and second jaw members at least one of which being movable relative to the other from a first position wherein the jaw members are disposed in spaced relation relative to one another to a second position wherein the jaw members cooperate to grasp tissue therebetween;
   each jaw member including a pair of spaced apart, electrically conductive tissue sealing surfaces extending along a length thereof, each tissue sealing surface adapted to conduct electrosurgical energy through tissue held therebetween to effect a tissue seal;
   an insulator disposed between each pair of electrically conductive sealing surfaces; and
   an electrically conductive cutting element disposed within each insulator and defining a geometrical configuration of a recurring pattern including a plurality of peaks, the recurring pattern having a period that is a multiple of an operating frequency of electrosurgical energy passed therethrough, the cutting elements adapted to electrosurgically effect a tissue cut.

2. An end effector assembly according to claim 1, wherein a number of the plurality of peaks is calculated based on a repetition of the peaks for a predetermined length of the electrically conductive cutting elements.

3. An end effector assembly according to claim 1, wherein the number of peaks for a given length of the cutting elements is a function of a wavelength of the operating frequency of the electrosurgical energy.

4. An end effector assembly according to claim 1, wherein the geometric configuration of the cutting element of the first jaw member is off-set from the geometric configuration of the cutting element of the second jaw member.

5. An end effector assembly according to claim 1, wherein the plurality of peaks of the cutting element of the first jaw member is configured to complement a plurality of valleys interposed between the plurality of peaks of the cutting element of the second jaw member.

6. A end effector assembly according to claim 1, wherein the electrically conductive cutting element disposed within the insulator on the first jaw member is disposed in general vertical registration to the insulator on the second jaw member;
   wherein the electrically conductive cutting element extends from the electrically conductive tissue sealing surface on the first jaw member towards the electrically conductive tissue sealing surface on the second jaw member to create a gap between the electrically conductive tissue sealing surfaces when the jaw members close for sealing tissue.

7. An end effector assembly according to claim 1, wherein the cutting elements are disposed in vertical registration relative to one another.

8. An end effector assembly for use with a bipolar forceps, the end effector assembly comprising:
   a pair of opposing first and second jaw members at least one of which being movable relative to the other from a first position wherein the jaw members are disposed in spaced relation relative to one another to a second position wherein the jaw members cooperate to grasp tissue therebetween;

each jaw member including a pair of spaced apart, electrically conductive tissue sealing surfaces extending along a length thereof, each tissue sealing surface adapted to conduct electrosurgical energy through tissue held therebetween to effect a tissue seal;

an insulator disposed between each pair of electrically conductive sealing surfaces; and an electrically conductive cutting element disposed within the insulator of the first jaw member and in general vertical registration with an electrically conductive cutting element disposed within the insulator of the second jaw member, each of the electrically conductive cutting elements including a plurality of peaks offset from a plurality of peaks of the other cutting element, wherein the number of peaks of at least one of the cutting elements is a function of a wavelength of an operating frequency of electrosurgical energy passed therethrough, the cutting elements adapted to electrosurgically effect a tissue cut, wherein the cutting elements are inactive during tissue sealing and the pair of spaced apart electrically conductive sealing surfaces on the first jaw member are energized to a different potential from the corresponding pair of spaced apart electrically conductive sealing surfaces on the second jaw member such that electrosurgical energy can be transferred through the tissue to effect a tissue seal.

9. An end effector assembly according to claim 8, wherein the plurality of peaks has a period that is a multiple of the operating frequency of the electrosurgical energy.

10. An end effector assembly according to claim 8, wherein the plurality of peaks of the cutting element of the first jaw member is configured to complement a plurality of valleys interposed between the plurality of peaks of the cutting element of the second jaw member.

11. An end effector assembly according to claim 8, wherein a number of the plurality of peaks is calculated based on a repetition of the peaks for a predetermined length of the electrically conductive cutting elements.

12. A method of manufacturing an electrically conductive cutting element adapted to be coupled to an end effector assembly for effecting a tissue cut, the steps comprising:

providing an electrically conductive electrode having a predetermined length; and calculating a number of peaks along the predetermined length and a period based on a repetition of the peaks, wherein the number of peaks is a function of an operating frequency of an energy source adapted to supply electrosurgical energy to the electrically conductive cutting element.

13. A method according to claim 12, wherein the period of the peaks is a multiple of the operating frequency.

* * * * *